United States Patent
Visconti et al.

(10) Patent No.: US 6,995,290 B2
(45) Date of Patent: Feb. 7, 2006

(54) SOLID MIXTURES OF ALPHA-HYDROXYCARBONYL DERIVATIVES OF ALPHA-METHYLSTYRENE OLIGOMERS AND THEIR USE

(75) Inventors: Marco Visconti, Varese (IT); Gabriele Norcini, Comabbio (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 54 days.

(21) Appl. No.: 10/475,065

(22) PCT Filed: Apr. 3, 2002

(86) PCT No.: PCT/EP02/03674

§ 371 (c)(1),
(2), (4) Date: Oct. 17, 2003

(87) PCT Pub. No.: WO02/085832

PCT Pub. Date: Oct. 31, 2002

(65) Prior Publication Data

US 2004/0116549 A1    Jun. 17, 2004

(30) Foreign Application Priority Data

Apr. 24, 2001 (IT) .......................... VA2001A0011

(51) Int. Cl.
*C07L 49/15* (2006.01)
(52) U.S. Cl. ........................................ 568/327
(58) Field of Classification Search ................. 568/327
See application file for complete search history.

(56) References Cited

U.S. PATENT DOCUMENTS 4,347,111 A * 8/1982 Gehlhaus et al. ............... 522/8
4,987,159 A   1/1991 Li Bassi et al. ............... 522/36

* cited by examiner

*Primary Examiner*—Michael L. Shippen
(74) *Attorney, Agent, or Firm*—Madan, Mossman & Sriram, P.C.

(57) ABSTRACT

The present invention refers to solid mixtures of alpha hydroxycarbonyl derivatives of alpha-methylstyrene oligomers containing at least 90% of the dimer isomers, the dimer isomer ratio being between 2.5 and 7, to their preparation and to their use as photoinitiators in photopolymerisation.

5 Claims, No Drawings

SOLID MIXTURES OF ALPHA-HYDROXYCARBONYL DERIVATIVES OF ALPHA-METHYLSTYRENE OLIGOMERS AND THEIR USE

The present invention refers to solid mixtures of alpha-hydroxycarbonyl derivatives of alpha-methylstyrene oligomers and to their use as photoinitiators in light-induced radical photopolymerisation of acrylic systems.

In particular the invention refers to the preparation of the solid mixtures, which can be easily handled and which mainly contain one of the dimer isomers.

According to a fundamental aspect of the invention it was surprisingly found that the solid mixtures exhibit a higher reactivity than the one expected from the to purity of the dimer isomers.

The use of oligomeric photoinitiators in the photopolymerisation has several advantages in comparison to the use of monomeric photoinitiators, such as a lower migratability of the photoinitiator from the formulation and a reduced amount of volatile compounds derived from their photodecomposition.

Those characteristics are important for the industrial use because they reduce the risk of contamination of the finished product with unwanted compounds.

Among oligomeric photoinitiators the alpha-hydroxycarbonyl derivatives of dimers and trimers of alpha-methylstyrene are known.

These photoinitiators are described, for instance, in U.S. Pat. No. 4,987,159.

They are mainly constituted by a mixture of dimer and trimer isomers.

At room temperature the mixture is a very highly viscous product that cannot be easily used as such in industrial applications.

In the present text with the expression "alpha-hydroxycarbonyl derivatives of oligomers of alpha-methylstyrene" we refer to compounds of Formula I, wherein n is a number equal or greater than 0.

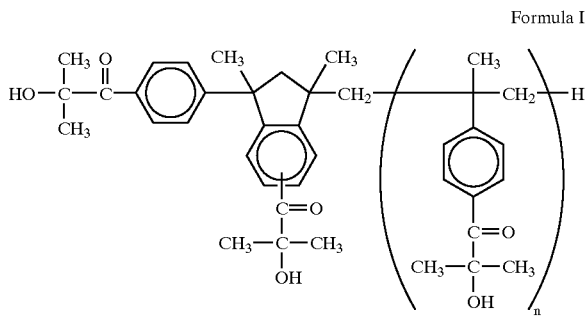

Formula I

The alpha-hydroxycarbonyl derivatives of oligomers of alpha-methylstyrene are a product with a pour point of from 40 to 50° C. In the present text, this product is indicated as "high viscosity mixture".

Another aspect of the invention is a process for the precipitation of a solid mixture from said high viscosity mixture.

According to another aspect of the invention the solid mixture obtained by precipitation from the high viscosity mixture mainly consists of the dimer isomers in a modified ratio.

In particular the concentration of dimer isomers 5 and 6 increases from 60–85% (w/w) in the high viscosity mixture to about 90–98% (w/w) in the solid mixture and the ratio of the dimer isomers 5 and 6 from 1.5–2.3 to 2.5–7.0.

The expression "dimer isomer 5" refers to the product of Formula II.

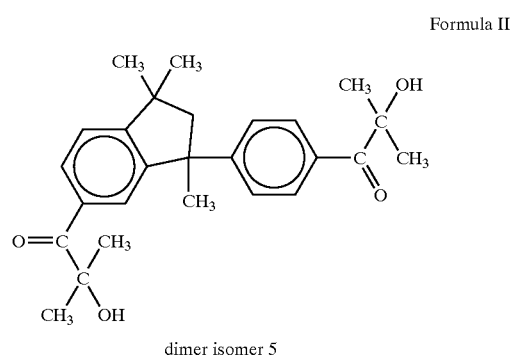

Formula II dimer isomer 5

The expression "dimer isomer 6" refers to the product of Formula III.

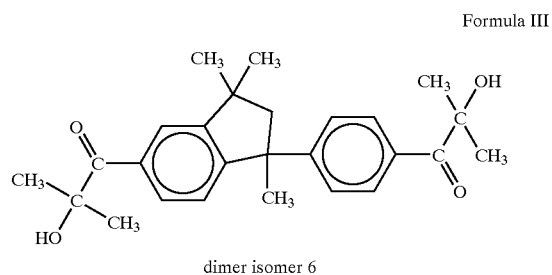

Formula III dimer isomer 6

In patent U.S. Pat. No. 4,987,159, the Applicant describes a precipitation of the mixture of alpha-hydroxycarbonyl derivatives of dimers and trimers of alpha-methylstyrene, without reporting a modification of the ratio between the dimer isomers 5 and 6 in the obtained mixture.

According to a fundamental aspect of the present invention, the solid mixtures of alpha-hydroxycarbonyl derivatives of oligomers of alpha-methylstyrene containing at least 90% of the dimer isomers 5 and 6 are disclosed, the ratio of the dimer isomer 5 and the dimer isomer 6 being between 2.5 and 7.

Another aspect of the present invention is a process for the preparation of the to solid mixtures exhibiting a higher reactivity than the one due to the increase in purity.

This behavior suggests that the reactivity of the dimer isomers is regiospecific.

The solid mixtures of alpha-hydroxycarbonyl derivatives of oligomers of alpha-methylstyrene of the present invention are obtained by precipitation from a high viscosity mixture containing at least 60% of the dimer isomers of the above mentioned derivatives.

Such a high viscosity mixture can be prepared as reported for instance in U.S. Pat. No. 4,987,159.

The process for the preparation of the solid mixtures of alpha-hydroxycarbonyl derivatives of oligomers of alpha-methylstyrene of the present invention consists in dissolving the high viscosity mixture of alpha-hydroxycarbonyl derivatives of oligomers of alpha-methylstyrene in a solvent with a polarity between 0.1 and 0.7, preferably between 0.25 and 0.6, with a ratio solvent/high viscosity mixture between 0.2 and 4, preferably between 0.4 and 2.5, keeping the solution at a temperature below 40° C. for from 10 to 60 hours and collecting the thus obtained solid mixture.

The polarity of the solvent ($\epsilon°$) corresponds to the absorption energy measured on $Al_2O_3$.

According to a further aspect of the invention the use in radical photopolymerisation of formulations containing at least one unsaturated compound of the solid mixtures of alpha-hydroxycarbonyl derivatives of oligomers of alpha-methylstirene, containing at least 90% of the dimer isomers 5 and 6, the ratio of the dimer isomers 5 and 6 being between 2.5 and 7 is disclosed.

The solid mixtures of the present invention are particularly suitable in photopolymerisation of formulations containing unsaturated compounds of the class of acrylic or methacrylic derivatives, or mixtures thereof, and are preferably used as photoinitiators in low yellowing paints and lacquers, in adhesives, in photocrosslinkable compositions for printing plates and in the field of graphic arts.

The isomer 5 has a higher reactivity than the isomer 6 in photopolymerisation. Such higher reactivity is demonstrated by the fact that the increase of the solid mixture of the invention is higher of at least 2% than the increase of the content of dimer isomers in the same mixture.

This is a surprising result, because at our knowledge a regiospecific activity had never been found before in photoinitiators.

In the following examples the measurement of the content of the dimer isomers and of the ratio between the two dimer isomers 5 and 6 in the high viscosity mixtures and in the solid mixtures reported in examples was carried out by HPLC (high performance liquid chromatography). The chromatographic 20 conditions were: column C18, 4 $\mu$m, 150×3.9 mm; eluent: solvent A=methanol, solvent B=water; gradient from 70% A to 100% A in 10 min. 100% A 10 min; flow rate 0.8 ml/min, detector UV 254 nm.

EXAMPLE 1

The precipitation of the solid mixture is carried out with toluene as solvent ($\epsilon°$ 0.29) using a high viscosity mixture with a dimer content of 85.1% and a ratio between the dimer isomers 5 and 6 of 1.93. This high viscosity mixture (Mixture 1) was obtained as reported in Example 10 of the patent U.S. Pat. No. 4,987,159.

14 kg of toluene are transferred into a heated reactor, set at a temperature of 120° C., and 28 kg of Mixture 1 are added under stirring. After complete dissolution the temperature is set at 20° C. and a small portion of a previously precipitated product is added.

The precipitation mixture is left at 20° C. under stirring for 48 hours. The precipitate is filtered on a buckner and washed twice with toluene.

The amount of dried precipitate is 11.8 kg (Solid Mixture 1, yield 41.3%); the content of the dimer isomers is 96.8% and the ratio of the dimer isomers 5 and 6 is 2.93

EXAMPLE 2

The precipitation of the solid mixture is carried out using ethyl acetate ($\epsilon°$ 0.58) as solvent and according to Example 1, using 1000 g of Mixture 1 and 500 g of ethyl acetate, at a dissolution temperature of 75° C., and at a precipitation temperature of 22–24° C. for 48 hours.

The amount of dried precipitate is 451 g (Solid Mixture 2, yield 45.1%); the content of the dimer isomers is 93.2% and the ratio between the dimer isomers 5 and 6 is 2.5.

EXAMPLE 3

Evaluation of the Photopolymerisation Reactivity of Solid Mixture 1

A formulation based on 75% (w/w) of Ebecryl 220 (urethane acrylate oligomer from UCB), 12.5% (w/w) of propoxylated glycerol triacrylate and 12.5% (w/w) of hexanediol diacrylate was prepared and 4% (w/w) of Solid Mixture 1 was added under stirring at room temperature.

A layer of 50 $\mu$m of the photoinitiated formulation was spread on a cardboard and cross-linked using a Giardina® apparatus equipped with a medium pressure mercury lamp of 80 W/cm. The maximum speed of cross-linking was 17.0 m/min. The photopolymerisation is considered complete when the formulation resists surface abrasion (it is not damaged after repeated z brushing using a sheet of paper pressed by a thumb).

EXAMPLE 4

Evaluation of the Photopolymerisation Reactivity of Mixture 1

A formulation based on 75% (w/w) of Ebecryl 220 (urethane acrylate oligomer from UCB), 12.5% (w/w) of propoxylated glicerol triacrylate and 12.5% (w/w) of hexanediol diacrylate was prepared and 4% (w/w) of Mixture 1 was added under stirring at room temperature.

A layer of 50 $\mu$m of the photoinitiated formulation was spread on cardboard and cross-linked using a Giardina( apparatus equipped with a medium pressure mercury lamp of 80 W/cm. The maximum speed of cross-linking, measured according to Example 3, was 14.5 m/mint s Comparing the results of Examples 3 and 4, an increase of content of the dimer isomers of 13.7% results in an increase of reactivity of 17.2%.

Comparing the results of Examples 3 and 4, an increase of content of the dimer isomers of 13.7% results in increase of reactivity of 17.2%.

This difference shows a surprisingly higher reactivity of isomer 5 compared to isomer 6.

The invention claimed is:

1. A composition comprising solid mixtures of alpha-hydroxycarbonyl derivatives of oligomers of alpha methylstyrene wherein the solid mixtures of alpha-hydroxycarbonyl derivatives of oligomers of alpha methylstyrene contain at least 90% of dimer isomers 5 and 6, and the ratio of the dimer isomer 5 and the dimer isomer 6 is from about 2.5 to about 7; wherein dimer isomer 5 has the structure:

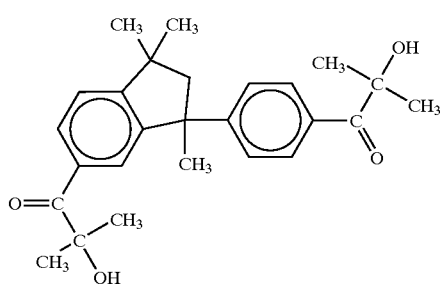

and wherein dimer isomer 6 has the structure:

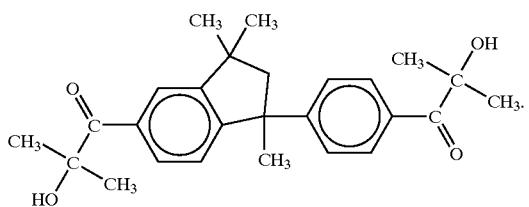

2. The composition of claim 1 wherein the solid mixtures of alpha-hydroxycarbonyl derivatives of oligomers of alpha methylstyrene are prepared by precipitation from a mixture containing them.

3. The composition of claim 2 wherein the mixture from which the solid mixtures of alpha-hydroxycarbonyl derivatives of oligomers of alpha methylstyrene are precipitated contains at least 60% of the dimer isomers 5 and 6.

4. A process for preparing solid mixtures of alpha-hydroxycarbonyl derivatives of oligomers of alpha-methylstyrene wherein the solid mixture contains at least 90% of dimer isomers 5 and 6 and the ratio of the dimer isomer 5 and the dimer isomer 6 is from about 2.5 to about 7, comprising dissolving a high viscosity mixture of alpha-hydroxycarbonyl derivatives of oligomers of alpha-methylstyrene in a solvent with a polarity of from about 0.1 to about 0.7 and with a ratio of solvent to mixture of from about 0.2 to about 4; keeping the solution at a temperature below about 40° C. for from about 10 to about 60 hours; and collecting the thus obtained solid mixture.

5. A process for photopolymerisation of formulations containing at least one unsaturated compound comprising admixing a composition of claim 1 and an formulation including at least one unsaturated compound under conditions sufficient to photopolymerise the formulation.

* * * * *